United States Patent [19]

Holm

[11] 4,283,549
[45] Aug. 11, 1981

[54] METHOD OF PRODUCING ALKANDIOL-DIAMINOBENZOATES

[75] Inventor: Boris Holm, Karlskoga, Sweden

[73] Assignee: Aktiebolaget Bofors, Bofors, Sweden

[21] Appl. No.: 966,404

[22] Filed: Dec. 4, 1978

[30] Foreign Application Priority Data

Dec. 12, 1977 [SE] Sweden ............................ 7714047

[51] Int. Cl.$^3$ ........................................... C07C 101/62
[52] U.S. Cl. ......................................... 560/50; 528/64
[58] Field of Search ................................... 560/19, 50

[56] References Cited

U.S. PATENT DOCUMENTS

| | | | |
|---|---|---|---|
| 3,037,046 | 5/1962 | Illich et al. | 560/19 |
| 3,891,693 | 6/1975 | Preston | 560/20 |
| 3,932,360 | 1/1976 | Cerankowski et al. | 528/64 X |

FOREIGN PATENT DOCUMENTS 2419322 11/1974 Fed. Rep. of Germany ............ 560/19

OTHER PUBLICATIONS

Weissberger, Separation & Purification, vol. III, 2d ed., Interscience Publ., Inc., N. Y., pp. 301–307, (1956).
Fieser, Experiments in Organic Chem., 3d Ed., D. C. Heath & Co., Boston, pp. 47–50, (1955).

*Primary Examiner*—G. T. Breitenstein
*Attorney, Agent, or Firm*—Pollock, Vande Sande & Priddy

[57] ABSTRACT

A method of producing alkandiol-diaminobenzoates which includes esterifying nitro-benzoic acid and certain diols in a melt and then dissolving the intermediate in a solvent sparingly soluble in water such as an aromatic hydrocarbon, an ether or an ester and reducing with hydrogen gas.

9 Claims, 1 Drawing Figure

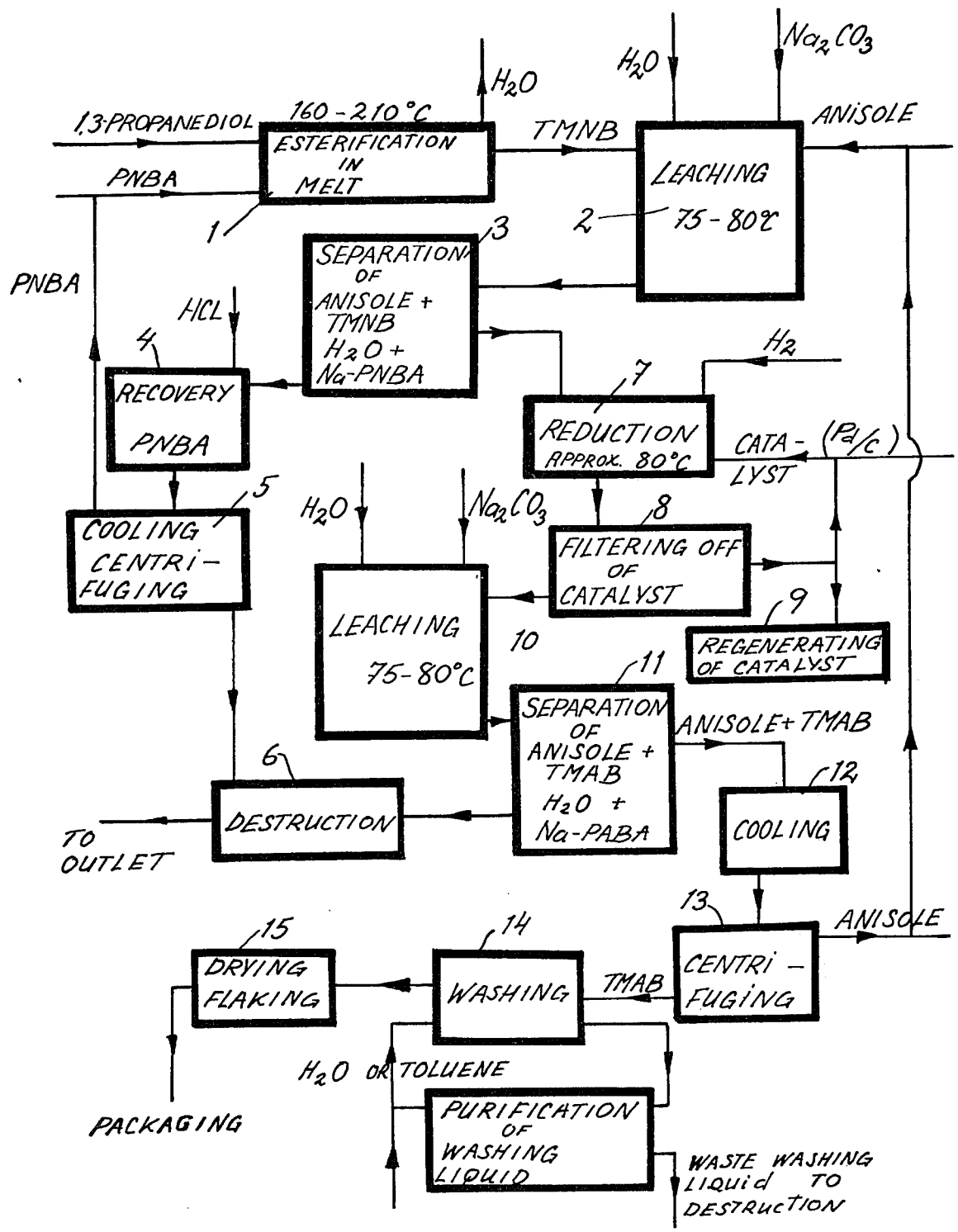

METHOD OF PRODUCING ALKANDIOL-DIAMINOBENZOATES 1,3-propanediol-di-p-aminobenzoate (TMAB) is a new type of cross-linker for polyurethanes intended to supersede the previously much used cross-linker bearing the designation MOCA and which now is possibly suspected of being carcinogenic.

For the production of TMAB, in principle the following general method has hitherto been applied for the production of alkandiol-diaminobenzoates.

As a starting chemical, p-nitro-benzoyl chloride has then been used, which has been made from the generally available industrial chemical p-nitro-benzoic acid (PNBA) and a chlorination reagent, usually thionyl chloride. The p-nitro-benzoyl chloride is reacted in pyridine as a solvent with 1,3-propanediol (trimethylene glycol) which gives 1,3-propanediol-di-p-nitrobenzoate (TMNB).

When the reaction has been completed, the quantity of pyridine and the hydrochloric acid formed during the reaction in the form of pyridine hydrochloride must be removed, which in itself does not pose any actual problems, but for which extra process steps are required.

When the pyridine and the hydrochloric acid have been removed and the reaction product has been isolated, this is dissolved in an appropriate solvent such as ethanol, after which a conventional reduction with hydrogen gas is carried out, using Pd/C as a catalyst. The final product then obtained is thereafter isolated through cooling and filtering, and is purified in a known way.

The state of the art of engineering is further described in the U.S. Pat. No. 3,932,360.

The present invention relates to a new, simplified method of producing alkandiol-diaminobenzoates through the reaction of a nitro-benzoic acid direct with an end position substituted diol with 2-6 methylene groups.

According to the present invention, the nitro-benzoic acid is thus reacted direct in the melt with an end position substituted diol to the corresponding dinitro ester, after which this is dissolved in anisole or some other solvent sparingly soluble in water and is reduced with hydrogen gas using Pd/C as a catalyst.

The method according to the invention has a plurality of advantages. Among other things, the introductory production of p-nitro-benzoyl chloride is eliminated, and the undesirable formation of hydrochloric acid at the reaction with the diol is avoided. In order that it shall be possible to esterify the p-nitro-benzoic acid direct in the melt, in comparison with the earlier technique, an increase in temperature in the esterification step is required from approx. 100°–110° C. to 160°–210° C. at the same time as the pyridine additive previously used can be eliminated entirely. Up to this point of the reaction process, two steps have thus been gained, viz. the production of the acid chloride and the requirement for a separation of the pyridine and the hydrochloric acid from the dinitro-benzoic acid ester.

The use of anisole as a solvent in the final hydrogen gas reduction has a plurality of substantial advantages, since the desired final product TMAB has a very temperature-dependent solubility in anisole. The solubility of TMAB in anisole is thus at 80° C. approx. 30%, while at 20° C. it is already down to a mere 2%. It is thus very easy to isolate TMAB dissolved in anisole through cooling. A further essential requirement for the method according to the invention which is fulfilled by anisole is that this is practically entirely insoluble in water, and therefore can easily be separated off simply through a forming of layers.

Other conceivable solvents in connection with the hydrogen gas reduction which at least reasonably fulfil the requirements of being sparingly soluble in water and readily soluble at an elevated temperature of the TMAB formed at the reduction are in addition to anisole, which well fulfils the requirements, other aromatic hydrocarbons such as toluene or xylene or certain ethers such as dibutyl ether, diisopropyl ether or certain esters such as ethyl acetate. However, none of these last-mentioned solvents are as appropriate as anisole, since TMAB is substantially more sparingly soluble in these than in anisole at the temperatures which come into question and therefore the capacity of the process would in that case be reduced considerably.

The above-mentioned state of the art of engineering if only the components essential for the final product are included, could thus be written:

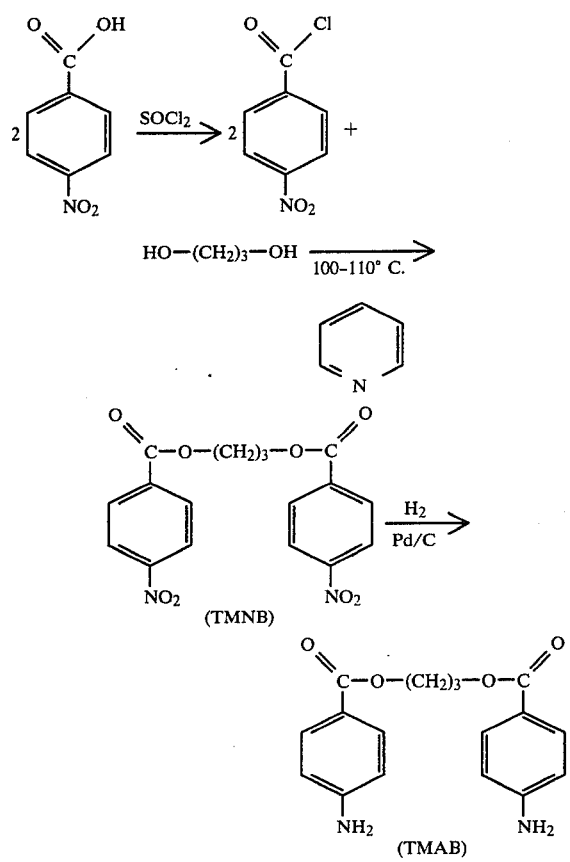

In the corresponding way, the general formula for the production of TMAB according to the method characteristic for the invention could be written:

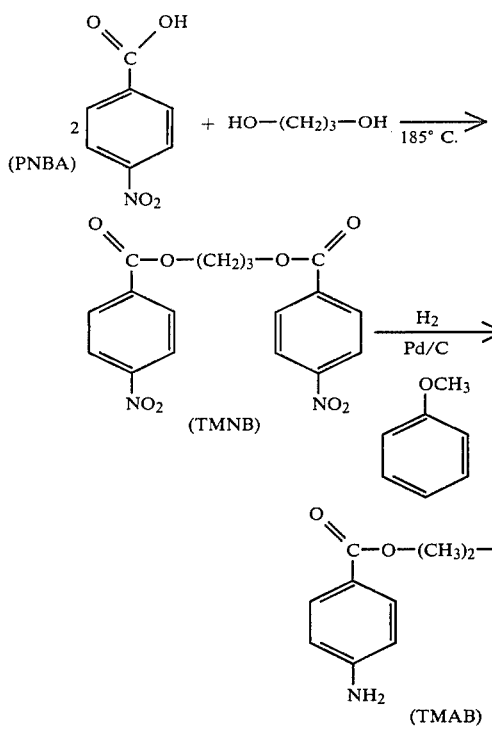

With the method according to the invention, an up to 50% (preferably approx. 10–25%) excess of p-nitro-benzoic acid (PNBA) is charged, as there will otherwise be formed at least a certain quantity of the undesirable monoester.

By adding water and sodium carbonate in connection with or immediately after the melt obtained at the esterification, which may possibly first have been solidified, is dissolved in anisole, the excess of PNBA is converted into its Na salt which is readily soluble in water but sparingly soluble in anisole. Through a forming of layers of the anisole-water phases, these are separated off with the components dissolved in them, i.e. TMNB and Na-PNBA.

Through a conventional acidification of the water solution of Na-PNBA the PNBA excess is recovered and can be returned to the starting step.

In connection with the final purification of the alkandioldiaminobenzoate obtained it is possible to utilize the condition that the product is sparingly soluble in toluene which, however, readily dissolves any impurities that may occur.

As a rule, however, a careful washing with water is sufficient.

From the general flow chart shown in the figure, it will be noted that at the esterification carried out at point 1 p-nitro-benzoic acid (PNBA) and 1,3-propanediol is added, of which the first-mentioned component, as previously intimated, should appropriately be charged in a stoichiometric excess of up to 50%, preferably 10–25%, in order to avoid a formation of the corresponding undesirable monoester. For carrying out the esterification, which thus takes place in a melt, a temperature of 160°–210° C. is required, at the same time as efficient stirring must be arranged. This involves that the entire quantity of PNBA and diol cannot be charged all at one time without any extra artifice, as the stirring of the mixture would in that case be practically impossible at low temperatures.

There are then two ways in which to proceed. The PNBA is either charged in portions to the diol, during a comparatively long time, with successive heating, and the second alternative is to charge all of the PNBA and diol and also an appropriate solvent, such as anisole or some other solvent with a boiling point within the interval of 130°–180° C. such as xylene or cumene and successively boil off the solvent while the temperature rises. The water formed at the esterification is conveyed off successively, and can be used as a measure of when the reaction has been completed. It takes several hours to carry out the esterification. The purpose of the solvent in this alternative is to facilitate the heat transfer in the heating stage.

The alternative of starting up the reaction with the aid of a solvent is described in example 1.

The 1,3-propanediol-di-p-nitro-benzoate (TMNB) formed at the esterification is dissolved in anisole or some other previously described at least partly comparable solvent at point 2 in the flow chart, and is leached with water while at the same time a base such as sodium carbonate or sodium hydrogen carbonate is added to convert the excess of benzoic acid into the corresponding salt which is readily soluble in water. A temperature of 75°–80° C. should be sufficient for the TMNB to have a satisfactory solubility in the anisole.

The anisole-water phases are conveyed on to separation at point 3, from where the water and the sodium salt of the benzoic acid is conveyed on to point 4 for recovery of the benzoic acid through acidification with HCl, cooling and centrifuging at point 5, from where the recovered PNBA is returned to step 1, while the residue is conveyed to point 6 for destruction and outlet. The destruction in question can be carried out as a combustion or an oxidation in a tube with nitric acid.

The anisole plus the TMNB dissolved in it is conveyed on to reduction with hydrogen gas in the autoclave 7. This should preferably be carried out at approx. 80° C. with Pd/C as a catalyst at a hydrogen gas pressure of 2–12 kg/cm$^2$, preferably 5–10 kg/cm$^2$.

Filtering off of the catalyst from the 1,3-propanediol-di-aminobenzoate formed at the reduction and regeneration and return of the catalyst have been intimated in connection with steps 8 and 9.

At point 10 the anisole with the TMAB dissolved in it is again leached in water, with an addition of sodium carbonate. This leaching can be considered as being unnecessary, in principle, but is a safety measure in order to remove the last residue of the excess of p-nitro-benzoic acid at 11, this time in the form of the water-soluble sodium salt of the p-aminobenzoic acid.

At 12 the TMAB is crystallized out of the anisole through cooling. At 13 the anisole is centrifuged off and can, in principle, be returned for use again in step 2 to dissolve the melt from esterification step 1.

From 13 the TMAB is conveyed on to washing, i.e. careful washing either with toluene or water. Purification of the washing liquid has been intimated at 16, while point 15 indicates drying and/or flaking or, alternatively, granulation of the purified TMAB which is thereafter ready for packaging.

The method according to the invention has been defined in the accompanying claims, and will now be somewhat further described in connection with the following examples.

EXAMPLE 1

1,3-propanediol-di-p-nitrobenzoate 200 g p-nitro-benzoic acid, 38 g 1,3-propanediol and 100 g anisole were charged in a flask. During stirring and heating to 185±5° C. the anisole and the water formed were distilled off. The stirring was continued at 185° C. for approx. 6 hours, or until no more water was distilled off. The melt in the flask was thereafter poured out on to a plate where it was allowed to solidify. The product thus obtained, which it was established was 1,3-propanediol-di-p-nitrobenzoate containing some p-nitro-benzoic acid had a weight of 219 g. When run on a larger scale, the product obtained can appropriately be flaked.

EXAMPLE 2

1,3-propanediol-di-p-nitrobenzoate

Same as above, but instead of anisole, xylene or cumene was added at the beginning of the esterification. The isolated product had a weight of 218 g.

EXAMPLE 3

1,3-propanediol-di-p-nitrobenzoate

To 38 g 1,3-propanediol was charged during heating and stirring 192 g p-nitro-benzoic acid in portions so that good stirring could be maintained. Thereafter the stirring was continued for approx. 6 hours at approx. 185° C., and the reaction water was distilled off. The 210 g melt then obtained was poured out on a plate. It was found to consist of TMNB+PNBA. It could have been dissolved directly in anisole for reduction to the amino compound described below.

EXAMPLE 4

1,3-propanediol-di-p-aminobenzoate

To the 219 g nitro ester obtained according to example 1 above was added 450 ml anisole, 500 ml water and 15 g sodium carbonate. The mixture was heated to approx. 80° while stirring for a few minutes. Thereafter the water and anisole phases were allowed to separate. The anisole phase was conveyed to an autoclave for reduction. Thereafter 1.3 g 5% Pd/C was added, as a catalyst.

The reduction was thereafter carried out at approx. 80° C. and 10 kg/cm° during a total time of approx. 1.5 hours.

The catalyst was filtered off and 150 ml hot water containing 1 g sodium carbonate was added while stirring. Thereafter the mixture was cooled to 5°-10° C. The precipitated crystals were filtered off, washed with water, and dried. A yield of 1,3-propanediol-di-p-aminobenzoate of 88% was obtained counted on the consumed p-nitro-benzoic acid (melting point 125°-127° C).

The excess of charged p-nitro-benzoic acid was recovered through acidification of the water phase from the first leaching. The p-nitro-benzoic acid thus obtained was recirculated to the next esterification batch. After drying, 32 g p-nitro-benzoic acid had been recovered in this way.

EXAMPLE 5

1,3-propanediol-di-p-aminobenzoate

The esterification was carried out as above, but after the reaction had been completed the anisole was added to the melt without foregoing crystallization of same. A solution of nitro ester and p-nitro-benzoic acid was thereby obtained in the anisole. This was followed by leaching and reduction in the same way as the reduction described above. 1,3-propanediol-di-p-aminobenzoate was obtained in an 87% yield counted on the p-nitro-benzoic acid consumed.

EXAMPLE 6

1,3-propanediol-di-p-aminobenzoate 1,3-propanediol-di-p-nitrobenzoate produced in a previously known way from p-nitro-benzoyl chloride and 1,3-propanediol was reduced in anisole to the corresponding amino compound in the same way as above with a 96% yield counted on the nitro ester charged.

EXAMPLE 7 (Pilot plant scale)

1,3-propanediol-di-p-aminobenzoate

At this test, the charge consisted to begin with of 100 kg p-nitro-benzoic acid, 19 kg 1,3-propanediol and 80 kg anisole. The temperature was raised successively while stirring to 185±5° C. and was maintained unchanged during 7 hours while stirring. The anisole and the water formed successively during the reaction was then allowed to be distilled off, and was recovered. The water phase proved to constitute 8.9 liters.

The melt obtained was dissolved in 315 kg anisole and leached in the way previously described at approx. 90° C. with 200 liters of water to which had been added 9 kg sodium carbonate.

After the leaching, the anisole and water phases were separated, and from the latter, in the way previously described, 17 kg p-nitro-benzoic acid was recovered, which corresponds to the entire excess charged.

The anisole phase was reduced with hydrogen gas at 80°-90° C. while 0.65 kg 5% Pd/C was added at a pressure of approx. 5 kg/cm². The reduction was entirely completed after about 1 hour.

Thereafter the catalyst was filtered off and the anisole phase was leached with 25 liters of water to which had been added 0.5 kg sodium carbonate. After stirring for a while, the phases were separated. The anisole phase was cooled and the 1,3-propanediol-di-p-aminobenzoate formed was separated off. The melting point determined for the product obtained was 126°-127° C. The calculated yield on the quantity of p-nitro-benzoic acid consumed was 86%.

I claim:

1. A method of producing 1,3 propanediol-di-p-aminobenzoate from p-nitro-benzoic acid and 1,3 propanediol, characterized in that the nitrobenzoic acid and the diol are esterified in a melt at 160°-210° C. after which the intermediate obtained is dissolved in the solvent anisole and is reduced with hydrogen gas in the presence of said solvent to the amino compound desired.

2. A method according to claim 1, characterized in that the nitrobenzoic acid is charged in a stoichiometric excess of up to 50%, and that the intermediate dissolved in the solvent is leached in water while adding a base selected from the group of sodium carbonate or sodium hydrogen carbonate in a stoichiometric excess compared with the original excess of nitrobenzoic acid and that the excess of nitrobenzoic acid is recovered from the sodium salt which is soluble in water thereby formed through acidification of the water separated from the solvent with the Na salt of the nitrobenzoic acid therein dissolved.

3. A method according to claim 1 or 2 characterized in that the desired amino compound is obtained from the solvent after this has been separated from the water through cooling and centrifuging.

4. A method according to claim 1 or 2 characterized in that the esterification of the nitro-benzoic acid with the diol is started up by all of the nitro-benzoic acid and solvent being added to the entire quantity of diol at one and the same time and that the temperature thereafter is successively raised while solvent and water formed at the reaction is successively permitted to be distilled off.

5. A method according to claim 1 or 2 characterized in that at the esterification the nitro-benzoic acid is charged in portions to the diol with good stirring and heating during such a long time that good stirring actually can take place during the entire process.

6. A method of producing 1,3-propanediol-di-p-aminobenzoate according to claim 1 or 2, characterized in that a stoichiometric excess of p-nitro-benzoic acid is esterified with 1,3-propanediol (trimethylene glycol) at a temperature of 160°–200° C., after which the product thereby obtained is dissolved in anisole and is leached in water while adding a stoichiometric excess of sodium carbonate or sodium hydrogen carbonate in relation to the excess of nitro-benzoic acid after which the solvent and water phases are separated from each other and the solvent phase then being reduced at 60°–130° C., with hydrogen gas while adding Pd/C as a catalyst and a hydrogen gas pressure of 2–12 kg/cm$^2$, after which the product thereby obtained is isolated from the solvent phase through cooling and centrifuging.

7. The method of claim 2 wherein the nitrobenzoic acid is charged in a stoichiometric excess of about 10–25%.

8. A method according to claim 3 characterized in that the esterification of the nitro-benzoic acid with the diol is started up by all of the nitro-benzoic acid and solvent being added to the entire quantity of diol at one and the same time and that the temperature thereafter is successively raised while solvent and water formed at the reaction is successively permitted to be distilled off.

9. The method of claim 6 wherein the p-nitro-benzoic acid is esterified at a temperature of 180°–190° C.; wherein the temperature of reducing is 70°–90° C. and said hydrogen gas pressure is 5–10 kg/cm$^2$.

* * * * *